United States Patent
Hapiot et al.

(10) Patent No.: US 10,138,200 B2
(45) Date of Patent: Nov. 27, 2018

(54) PROCESS FOR PREPARING POLYOLS

(71) Applicants: PIVERT S.A.S., Venette (FR); CENTRE NATIONAL DE LA RECHERCHE SCIENTIFIQUE (CNRS), Paris (FR); UNIVERSITE D'ARTOIS, Arras (FR)

(72) Inventors: Frederic Hapiot, Ennevelin (FR); Eric Monflier, La Madeleine (FR); Theodore Vanbesien, Lille (FR)

(73) Assignees: Pivert S.A.S., Venette (FR); Centre National De La Recherche Scientifique (CNRS), Paris (FR); Universite D'Artois, Arras (FR)

( * ) Notice: Subject to any disclaimer, the term of this patent is extended or adjusted under 35 U.S.C. 154(b) by 0 days.

(21) Appl. No.: 15/569,880

(22) PCT Filed: Jun. 15, 2016

(86) PCT No.: PCT/EP2016/063718
§ 371 (c)(1),
(2) Date: Oct. 27, 2017

(87) PCT Pub. No.: WO2017/001194
PCT Pub. Date: Jan. 5, 2017

(65) Prior Publication Data
US 2018/0127350 A1    May 10, 2018

(30) Foreign Application Priority Data
Jun. 30, 2015 (FR) ...................... 15 01373

(51) Int. Cl.
C11C 3/02 (2006.01)
C07C 31/22 (2006.01)
(Continued)

(52) U.S. Cl.
CPC .......... *C07C 67/347* (2013.01); *C07C 31/225* (2013.01); *C07C 69/675* (2013.01); *C11C 3/02* (2013.01)

(58) Field of Classification Search
CPC ........ C07C 67/347; C07C 31/225; C11C 3/02
(Continued)

(56) References Cited

U.S. PATENT DOCUMENTS 4,197,414 A    4/1980  Hartwell et al.
2005/0070620 A1    3/2005  Herrington

FOREIGN PATENT DOCUMENTS

EP    0014225 A1    8/1980
GB    2046266 A    11/1980
(Continued)

OTHER PUBLICATIONS

Hunter, Douglas L. et al., "Deactivation of Rhodium Hydroformylation Catalysts on Amine Functionalized Organic Supports ", Applied Catalysis (1985), pp. 275-285, vol. 19, Copyright Elsevier Science Publishers B.V. (1985); https://doi.org/10.1016/S0166-9834(00)81750-9.

(Continued)

*Primary Examiner* — Deborah D Carr
(74) *Attorney, Agent, or Firm* — Avery N. Goldstein; Blue Filament Law, PLLC

(57) ABSTRACT

The present invention relates to a process for preparing polyols. In particular, the present invention relates to the preparation, in a single step, of polyols by a process involving a hydrohydroxymethylation reaction starting from a composition A comprising one or more compounds of formula (I).

19 Claims, 3 Drawing Sheets

(I)

Catalyseur CO/H₂
NR⁶R⁷R⁸

(II)

(51) Int. Cl.
  *C07C 67/347* (2006.01)
  *C07C 69/675* (2006.01)
(58) Field of Classification Search
  USPC .......................................................... 554/173
  See application file for complete search history.

(56) References Cited

FOREIGN PATENT DOCUMENTS

WO      03093215 A1    11/2003
WO      2006012344 A1   2/2006

OTHER PUBLICATIONS

Cheung, Lawrence L.W. et al., "Synthesis of Alcohols via a Rhodium-Catalyzed Hydroformylation-Reduction Sequence using Tertiary Bidentate Amine Ligands", Advanced Synthesis & Catalysis (2012), pp. 2019-2022, vol. 354, Copyright Wiley-VCH Verlag GmbH & Co. KGaA, Weinheim (2012); DOI: 10.1002/adsc.201200053; http://www.asc.wiley-vch.de.

Torres, Galina Morales et al., "Production of Alcohols via Hydroformylation", Catalysis Science & Technology (2015), pp. 34-54, vol. 5, Copyright The Royal Society of Chemistry (2015); DOI: 10.1039/C4CY01131G; http://www.pubs.rsc.org/en/content/articlelanding/2015/cy/c4cy01131g#!divAbstract.

International Search Report dated Sep. 13, 2016 for International Application No. PCT/EP2016/063718 filed Jun. 15, 2016.

PROCESS FOR PREPARING POLYOLS

FIELD OF THE INVENTION

The invention relates to a process for preparing polyols, preferably starting from triglycerides. In particular, the invention relates to a process for preparing polyols, in a single step, by reductive hydroformylation or hydrohydroxymethylation reaction.

TECHNICAL BACKGROUND OF THE INVENTION

Polyols are generally produced from petroleum. Polyols are used in many fields of application, such as textiles, plastics, chemistry, the manufacturing industry or the cosmetics industry. Polyols are in particular used in the preparation of coatings, of adhesives, of elastomers, of resins or of foams.

Polyols are generally prepared via an alkene hydroformylation reaction. However, most of the processes described in the prior art regarding this type of approach use ligands that are difficult to handle in the open air, such as trialkylphosphines or phosphites which degrade in water. A simpler alternative consists in using amines as ligands. The use of tertiary amines has been described in the literature for converting terminal alkenes to alcohols by means of a reductive hydroformylation reaction (Morales Torres et al., Catal. Sci. Technol., 2015, 5, 34-54). Various systematic studies have shown the influence of amine, in terms of structure, of basicity and of amount, on the hydroformylation reaction with rhodium (Hunter et al., Appl. Catal., 1985, 19, 275-285). The most recent use of this type of catalytic system dates back to 2012 by Alper et al., (Adv. Synth. Catal., 2012, 354, 2019-2022) on the synthesis of terminal alcohols from styrene in the presence of tertiary diamines as ligand. The production of alcohol by this process using rhodium-amine catalytic systems has also been described in EP 0014225 and U.S. Pat. No. 4,197,414, but only starting from light olefins of 1-hexene type.

For heavier olefins, polyols are preferentially synthesized by an epoxidation reaction as described by WO 2006/012344.

SUMMARY OF THE INVENTION

The present invention allows the preparation of polyols from biobased compounds, for example from a vegetable oil. The process is particularly advantageous for the selective preparation of polyols from triglycerides with a high yield and high selectivity.

The present invention relates to a process for preparing polyols from a composition A comprising one or more compounds of formula (I)

wherein
$R^1$, $R^2$, $R^3$, $R^4$, $R^5$, $R^6$ and $R^7$ are, independently of one another, and for $R^3$ and $R^7$ independently for each of the n units, chosen from the group consisting of H, —$OR^{15}$, $C_1$-$C_{10}$ alkyl which is unsubstituted or substituted with one or more —$OR^{15}$ groups, $C_6$-$C_{12}$ aryl which is unsubstituted or substituted with one or more —$OR^{15}$ groups, or $C_3$-$C_{10}$ cycloalkyl which is unsubstituted or substituted with one or more —$OR^{15}$ groups, or a group of formula (Ia)

$R^{15}$ represents H or $C_1$-$C_{10}$ alkyl which is unsubstituted or substituted with one or more —OH groups;

a, b, x and y are independently of one another, independently for each group of formula (Ia), independently for each $[(CH_2)_a\!-\!C\!=\!C\!-\!(CH_2)_b]_r$ unit and independently for each $[(CH_2)_x\!-\!C\!=\!C\!-\!(CH_2)_y]_p$ unit, an integer between 0 and 20, advantageously between 0 and 15, preferably between 0 and 12;

r is an integer between 1 and 10, advantageously between 1 and 5;

p is an integer between 1 and 10, advantageously between 1 and 5;

n is an integer between 1 and 7;

said process comprising a step a) of placing together, with stirring and under an atmosphere of hydrogen and of carbon monoxide:

at least one precatalyst which is a complex comprising a transition metal chosen from column 9 of the periodic table of elements, a tertiary amine, or a non-quaternary ammonium salt thereof, of formula $NR^8R^9R^{10}$ wherein $R^8$, $R^9$ and $R^{10}$ represent, independently of one another, a $C_1$-$C_{10}$ alkyl, a $C_6$-$C_{12}$ aryl or a $C_3$-$C_{10}$ cycloalkyl, or $R^8$ and $R^9$ form, together with the nitrogen atom to which they are attached, a heterocycle comprising four, five or six ring members, and said composition A comprising one or more compounds of formula (I).

The present process allows the formation of one or more compounds derived from said one or more compounds of formula (I) wherein, for all or some of the carbon-carbon double bonds, a carbon atom of the carbon-carbon double bonds of the compound of formula (I) has been substituted with a —$CH_2OH$ group, the other carbon atom with this same carbon double bond being substituted with a hydrogen.

DETAILED DESCRIPTION OF THE PRESENT INVENTION

The term "substituted" as used in the present invention means that one or more hydrogen atoms of the group to which the term "substitute" refers is replaced with one of the substituents named, provided that the normal valency of the atom on which the substitution is considered is not exceeded and that the substitution results in a stable chemical compound, that is to say a compound that is sufficiently robust to be isolated from a reaction mixture.

The term "alkyl" refers to linear or branched hydrocarbon-based chains containing the specified number of carbon atoms. For example, $C_1$-$C_6$ alkyl means a linear or branched alkyl group containing at least 1 and at most 6 carbon atoms. The alkyl group can be substituted with an unsubstituted aryl group, halogen, $NO_2$, CN, $SO_3H$, OH, $C_1$-$C_{10}$ alkoxy, or a carbonyl or carboxyl group. The term "aryl" refers to an aromatic hydrocarbon-based ring containing the specified number of carbon atoms which is unsubstituted or substituted with an unsubstituted $C_1$-$C_{10}$ alkyl, halogen, $NO_2$, CN, $SO_3H$, or a carbonyl, carboxyl, OH or $C_1$-$C_{10}$ alkoxy group. For example aryl can be a phenyl, naphthyl, anthracyl or phenanthryl. The term "cycloalkyl" refers to a fused monocyclic or polycyclic, non-aromatic hydrocarbon-based ring comprising the specified number of carbon atoms. For example, cycloalkyl comprises cyclopropyl, cyclobutyl, cyclopentyl, cyclohexyl, cycloheptyl or cyclooctyl. The term "heterocycle" refers to a fused monocyclic or polycyclic, non-aromatic hydrocarbon-based ring comprising the specified number of ring members, wherein at least one of the carbon atoms is replaced with a phosphorus, sulfur, nitrogen or oxygen atom. In particular, the term heterocycle as used in the present invention refers to a fused monocyclic or polycyclic, non-aromatic hydrocarbon-based ring comprising the specified number of ring members and wherein at least one of the carbon atoms is replaced with a nitrogen atom.

According to the present invention, a process for preparing polyols is provided. The present process for preparing polyols is carried out starting from a composition A comprising one or more compounds of formula (I)

(I)

wherein
$R^1$, $R^2$, $R^3$, $R^4$, $R^5$, $R^6$ and $R^7$ are, independently of one another, and for $R^3$ and $R^7$ independently for each of the $[CR^3R^7]_n$ units, chosen from the group consisting of H, —$OR^{15}$, $C_1$-$C_{10}$ alkyl which is unsubstituted or substituted with one or more —$OR^{15}$ groups, $C_6$-$C_{12}$ aryl which is unsubstituted or substituted with one or more —$OR^{15}$ groups, or $C_3$-$C_{10}$ cycloalkyl which is unsubstituted or substituted with one or more —$OR^{15}$ groups, or a group of formula (Ia)

(Ia)

$R^{15}$ represents H or $C_1$-$C_{10}$ alkyl which is unsubstituted or substituted with one or more —OH groups;
a, b, x and y are, independently of one another, independently for each group of formula (Ia), independently for each $[(CH_2)_a$—C=C—$(CH_2)_b]_r$ unit and independently for each $[(CH_2)_x$—C=C—$(CH_2)_y]_p$ unit, an integer between 0 and 20, advantageously between 0 and 15, preferably between 0 and 12;
r is an integer between 1 and 10, advantageously between 1 and 5;
p is an integer between 1 and 10, advantageously between 1 and 5;
n is an integer between 1 and 7;
said process comprising a step a) of placing together, with stirring and under an atmosphere of hydrogen and of carbon monoxide:
at least one precatalyst which is a complex comprising a transition metal chosen from column 9 of the periodic table of elements,
a tertiary amine, or a non-quaternary ammonium salt thereof, of formula $NR^8R^9R^{10}$ wherein $R^8$, $R^9$ and $R^{10}$ represent, independently of one another, a $C_1$-$C_{10}$ alkyl, a $C_6$-$C_{12}$ aryl or a $C_3$-$C_{10}$ cycloalkyl, or $R^8$ and $R^9$ form, together with the nitrogen atom to which they are attached, a heterocycle comprising four, five or six ring members,
said composition A comprising one or more compounds of formula (I).

The carbon-carbon double bonds contained in the compound(s) of the formula (I), (Ia) or (II) as described in the present invention can be in the cis or trans configuration. The term "carbon-carbon double bond(s)" encompasses both configurations.

Figure 1:
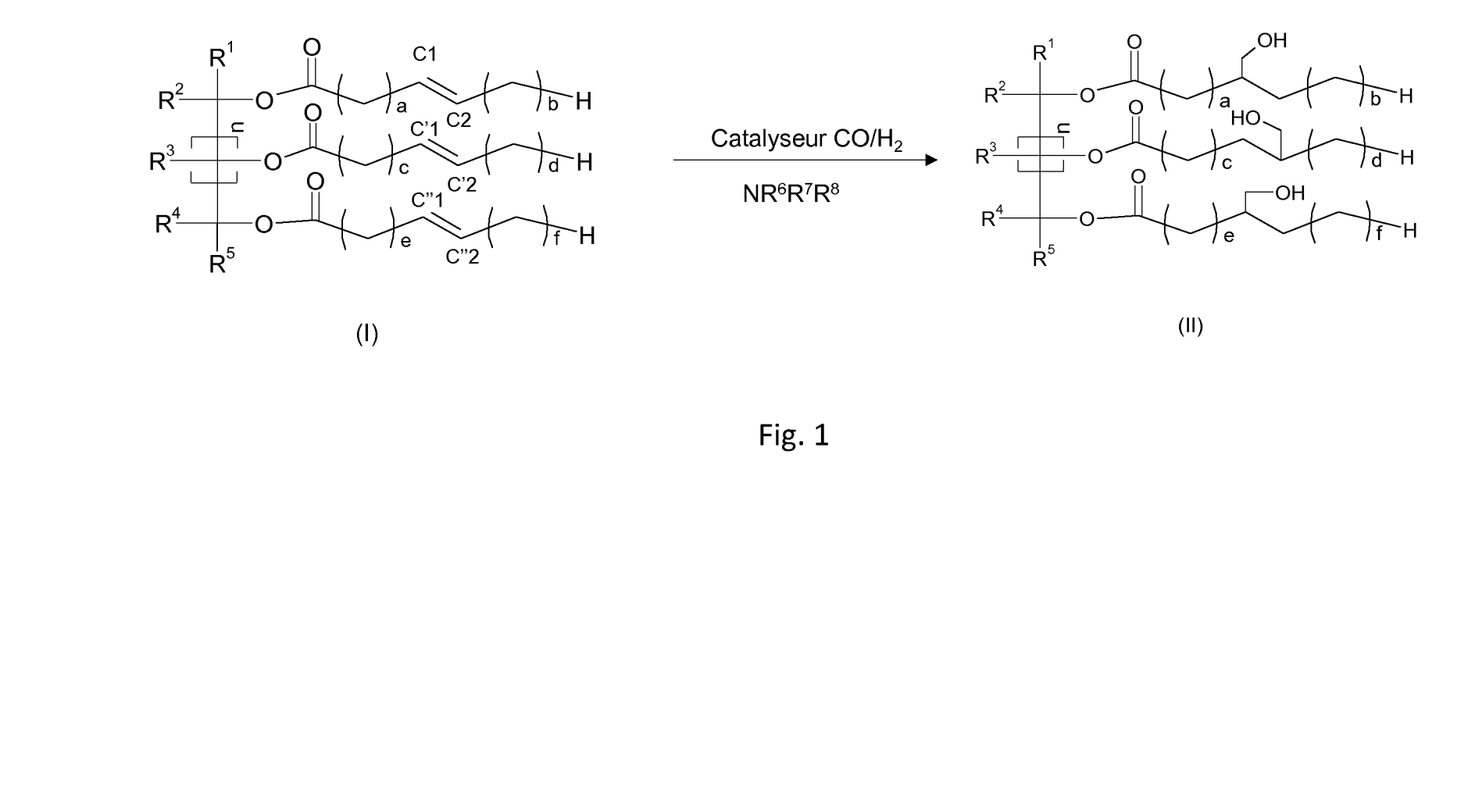
FIG. 1 represents a scheme of the synthesis of polyols according to one particular embodiment of the invention.

FIG. 1 illustrates the process according to one particular embodiment of the present invention involving a hydrohydroxymethylation reaction. The compound (I) is represented by triolein comprising three carbon-carbon double bonds. The process according to the present invention thus allows the preparation of a polyol wherein the three carbon-carbon double bonds are hydrohydroxymethylated. The —$CH_2OH$ group can be borne, for each of the carbon-carbon double bonds, by any one of the carbon atoms C1 or C2, C'1 or C'2, or C"1 or C"2.

According to one preferred embodiment, said composition A can comprise at least 20% by weight of said one or more compounds of formula (I) on the basis of the total weight of the composition A, advantageously at least 30% by weight, preferably at least 40% by weight, more preferentially at least 50% by weight, in particular at least 60% by weight, more particularly at least 70% by weight, preferably at least 80% by weight.

Preferably, a and x can be, independently of one another, independently for each group of formula (Ia), independently for each $[(CH_2)_a$—C=C—$(CH_2)_b]_r$ unit and independently for each $[(CH_2)_x$—C=C—$(CH_2)_y]_p$ unit, an integer between 1 and 12, advantageously between 2 and 10, preferably between 3 and 9, in particular between 3 and 8 and more particularly between 4 and 8.

Preferably, b and y can be, independently of one another, independently for each group of formula (Ia), independently for each $[(CH_2)_a$—C=C—$(CH_2)_b]_r$ unit and independently for each $[(CH_2)_x$—C=C—$(CH_2)_y]_p$ unit, an integer between 0 and 12, advantageously between 0 and 10, preferably between 0 and 9, in particular between 2 and 9, and more particularly between 3 and 8.

Preferably, n can be an integer between 1 and 7, advantageously between 1 and 5, preferably between 1 and 4, in particular between 1 and 3, and more particularly n is 1.

Preferably, p can be an integer between 1 and 5, advantageously between 1 and 4, preferably between 1 and 3. In particular, p is 1, 2 or 3, more particularly p is 1 or 2.

Preferably, r can be an integer between 1 and 5, advantageously between 1 and 4, preferably between 1 and 3. In particular, r is 1, 2 or 3, more particularly r is 1 or 2.

Advantageously, in said one or more compounds of formula (I), at least one of the substituents $R^1$, $R^2$, $R^3$, $R^4$, $R^5$, $R^6$ and $R^7$ is a group of formula (Ia). Preferably, in said one or more compounds of formula (I), at least two of the substituents $R^1$, $R^2$, $R^3$, $R^4$, $R^5$, $R^6$ and $R^7$ are a group of formula (Ia).

According to one preferred embodiment, said one or more compounds of formula (I) are of formula (II)

(II)

wherein
- a, b, x and y are, independently of one another, independently for each group of formula (Ia), independently for each $[(CH_2)_a\!-\!C\!=\!C\!-\!(CH_2)_b]_r$ unit and independently for each $[(CH_2)_x\!-\!C\!=\!C\!-\!(CH_2)_y]_p$ unit, an integer between 0 and 20, advantageously between 0 and 15, preferably between 0 and 12;
- r is an integer between 1 and 10, advantageously between 1 and 5;
- p is an integer between 1 and 10, advantageously between 1 and 5;
- n is an integer between 1 and 7, preferably between 1 and 4;
- $R^1$, $R^2$, $R^3$, $R^4$ and $R^5$ are, independently of one another, and for $R^3$ independently for each of the n units, chosen from the group consisting of H, $-OR^{15}$, a group of formula (Ia) as described above, $C_1$-$C_{10}$ alkyl which is unsubstituted or substituted with one or more $-OR^{15}$ groups, $C_6$-$C_{12}$ aryl which is unsubstituted or substituted with one or more $-OR^{15}$ groups, or $C_3$-$C_{10}$ cycloalkyl which is unsubstituted or substituted with one or more $-OR^{15}$ groups, wherein $R^{15}$ represents H or $C_1$-$C_{10}$ alkyl which is unsubstituted or substituted with one or more $-OH$ groups.

In said one or more compounds of formula (II), a and x can be, independently of one another, independently for each $[(CH_2)_x\!-\!C\!=\!C\!-\!(CH_2)_y]_p$ unit and independently for each $[(CH_2)_a\!-\!C\!=\!C\!-\!(CH_2)_b]_r$ unit, an integer between 1 and 12, advantageously between 2 and 10, preferably between 3 and 9, in particular between 3 and 8 and more particularly between 4 and 8.

In said one or more compounds of formula (II), b and y can be, independently of one another, independently for each $[(CH_2)_x\!-\!C\!=\!C\!-\!(CH_2)_y]_p$ unit and independently for each $[(CH_2)_a\!-\!C\!=\!C\!-\!(CH_2)_b]_r$ unit, an integer between 0 and 12, advantageously between 0 and 10, preferably between 0 and 9, in particular between 2 and 9, and more particularly between 3 and 8.

In said one or more compounds of formula (II), n can be an integer between 1 and 7, advantageously between 1 and 5, preferably between 1 and 4, in particular between 1 and 3, and more particularly n is 1.

In said one or more compounds of formula (II), p can be an integer between 1 and 5, advantageously between 1 and 4, preferably between 1 and 3. In particular, p is 1, 2 or 3, more particularly p is 1 or 2.

In said one or more compounds of formula (II), r can be an integer between 1 and 5, advantageously between 1 and 4, preferably between 1 and 3. In particular, r is 1, 2 or 3, more particularly r is 1 or 2.

Preferably, in said one or more compounds of formula (II), the substituents $R^1$, $R^2$, $R^3$, $R^4$ and $R^5$ can be, independently of one another, and for $R^3$ independently for each of the n units, chosen from the group consisting of H, $-OR^{15}$, a group of formula (Ia) as described above, $C_1$-$C_{10}$ alkyl which is unsubstituted or substituted with one or more $-OR^{15}$ groups, wherein $R^{15}$ represents H or $C_1$-$C_{10}$ alkyl which is unsubstituted or substituted with one or more $-OH$ groups.

In particular, in said one or more compounds of formula (II), the substituents $R^1$, $R^2$, $R^3$, $R^4$ and $R^5$ can be, independently of one another, and for $R^3$ independently for each of the n units, chosen from the group consisting of H, and $C_1$-$C_{10}$ alkyl which is unsubstituted or substituted with one or more $-OR^{15}$ groups, wherein $R^{15}$ represents H.

More particularly, in said one or more compounds of formula (II), the substituents $R^1$, $R^2$, $R^3$, $R^4$ and $R^5$ are a hydrogen.

Thus, according to one preferred embodiment, said one or more compounds are of formula (II) wherein
- a and x can be, independently of one another, independently for each $[(CH_2)_x\!-\!C\!=\!C\!-\!(CH_2)_y]_p$ unit and independently for each $[(CH_2)_a\!-\!C\!=\!C\!-\!(CH_2)_b]_r$ unit, an integer between 1 and 12, advantageously between 2 and 10, preferably between 3 and 9, in particular between 3 and 8 and more particularly between 4 and 8;
- b and y can be, independently of one another, independently for each $[(CH_2)_x\!-\!C\!=\!C\!-\!(CH_2)_y]_p$ unit and independently for each $[(CH_2)_a\!-\!C\!=\!C\!-\!(CH_2)_b]_r$ unit, an integer between 0 and 12, advantageously between 0 and 10, preferably between 0 and 9, in particular between 2 and 9, and more particularly between 3 and 8;
- $R^1$, $R^2$, $R^3$, $R^4$ and $R^5$ are a hydrogen;
- p is 1, 2 or 3 independently for each $[(CH_2)_x\!-\!C\!=\!C\!-\!(CH_2)_y]_p$ unit;
- r is 1, 2 or 3 independently for each $[(CH_2)_a\!-\!C\!=\!C\!-\!(CH_2)_b]_r$ unit;
- n is 1.

According to one particular embodiment of the present invention, said composition A can consist of one or more compounds of formula (I) or (II).

In the process according to the present invention, the tertiary amine can be of formula $NR^8R^9R^{10}$ wherein $R^8$, $R^9$ and $R^{10}$ represent, independently of one another, a $C_1$-$C_{10}$ alkyl, or $R^8$ and $R^9$ form, together with the nitrogen atom to which they are attached, a heterocycle comprising four, five or six ring members. Advantageously, the tertiary amine can be of formula $NR^8R^9R^{10}$ wherein $R^8$, $R^9$ and $R^{10}$ represent, independently of one another, a $C_1$-$C_{10}$ alkyl, or $R^8$ and $R^9$ form, together with the nitrogen atom to which they are attached, a heterocycle chosen from the group consisting of azetidine, diazetidine, pyrrolidine, imidazolidine, pyrazolidine, piperidine and piperazine. The imidazolidine and pyrazolidine heterocycles comprise two nitrogen atoms. In the case of the present invention, the two nitrogen atoms of these imidazolidine and pyrazolidine heterocycles are tertiary. Preferably, the tertiary amine can be of formula $NR^8R^9R^{10}$ wherein $R^8$, $R^9$ and $R^{10}$ represent, independently of one another, $C_1$-$C_{10}$ alkyl, or $R^8$ and $R^9$ form, together with the nitrogen atom to which they are attached, a pyrrolidine or a piperidine. In particular, the tertiary amine can be of formula $NR^8R^9R^{10}$ wherein $R^8$, $R^9$ and $R^{10}$ represent, independently of one another, a $C_1$-$C_6$ alkyl.

The tertiary amine can be supported on a resin. Thus, the substituent $R^{10}$ can be a spacer group between the nitrogen atom of the tertiary amine and the resin. $R^{10}$ can be a $C_1$-$C_{10}$ alkyl, a benzyl, a $C_6$-$C_{18}$ aryl or a $C_3$-$C_{10}$ cycloalkyl.

Preferably, said tertiary amine has a pKa greater than 6, advantageously greater than 7, preferably greater than 8, in particular greater than 9. Preferably, said tertiary amine has a pKa less than 15, advantageously less than 14, preferably less than 12, in particular less than 11. Said tertiary amine can thus have a pKa between 6 and 14, advantageously between 8 and 12, preferably between 9 and 11.

The present process is carried out under pressure of a hydrogen and carbon monoxide atmosphere. The pressure refers to the sum of the partial carbon monoxide and hydrogen pressures. The pressure can be between 50 bar and 200 bar, advantageously between 65 bar and 150 bar, preferably between 70 bar and 130 bar, in particular between 75 bar and 120 bar.

Preferably, the molar ratio between the carbon monoxide and the hydrogen can be between 2:1 and 1:10, advantageously the molar ratio between the carbon monoxide and the hydrogen is between 1:1 and 1:5, preferably the molar ratio is between 1:1 and 1:3, in particular the molar ratio between the carbon monoxide and the hydrogen is between 1:1 and 1:2.

Preferably, step a) of the present process can be carried out at a temperature between 60° C. and 200° C., advantageously between 70° C. and 180° C., preferably between 80° C. and 150° C.

Step a) of the present process can be carried out in the presence of an organic solvent such as aromatic or aliphatic hydrocarbons. For example, the solvent can be toluene, benzene, hexane or heptane.

As mentioned above, the process according to the present invention is carried out in the presence of at least one precatalyst. Said precatalyst is a complex comprising a transition metal chosen from column 9 of the periodic table of elements. Advantageously, said precatalyst is a complex comprising a transition metal chosen from cobalt or rhodium. Advantageously, the precatalyst is a complex comprising rhodium as transition metal and one or more ligands. Preferably, at least one of said one or more ligands is chosen from CO, acetylacetonate, cyclooctadiene, norbornene and acetate. The precatalyst can be supported on a solid support. The support can be carbon black, $SiO_2$, $Al_2O_3$, $TiO_2$, MgO, ZnO, $CaCO_3$, $CaSO_4$ or $MgSO_4$ or a combination thereof. The weight ratio between the support and the precatalyst can be between 1 and 100.

Preferably, the molar ratio between the tertiary amine of formula $NR^8R^9R^{10}$ as described above and the transition metal of the complex used as precatalyst in step a) of the present process is greater than 20, advantageously greater than 50, preferably greater than 100, in particular greater than 200.

Said one or more ligands can also comprise at least one monodentate or bidentate phosphorus-bearing ligand comprising at least one $C_6$-$C_{18}$ aryl substituent substituted in the ortho position with respect to the phosphorus atom or comprising at least one $C_6$-$C_{18}$ aryloxy substituent. Advantageously, said phosphorus-bearing ligand can be of formula $P(Ar)_3$ or $(Ar)_2$—P-L-P$(Ar)_2$ of which Ar is a $C_6$-$C_{18}$ aryl group substituted at least in the ortho position with respect to the phosphorus atom with a group selected from the group consisting of $C_1$-$C_6$ alkyl, phenyl, benzyl, $C_3$-$C_6$ cycloalkyl, halogen, $C_1$-$C_6$ alkoxyl and $C_6$ aryloxy; and L is a spacer arm selected from the group consisting of $C_1$-$C_6$ alkyl, $C_6$-$C_{12}$ aryl and $C_3$-$C_{10}$ cycloalkyl. The expression "substituted in the ortho position with respect to the phosphorus atom" means that, in the aryl ring, at least one of the two ortho positions with respect to the carbon atom bonded to the phosphorus atom is substituted with one of the groups mentioned. Preferably, said phosphorus-bearing ligand can be of formula $P(Ar)_3$ wherein Ar is a $C_6$-$C_{18}$ aryl group substituted in the ortho position with respect to the phosphorus atom with a group selected from the group consisting of methyl, ethyl, methoxy, phenyl, benzyl, —F and cyclohexyl.

Alternatively, said phosphorus-bearing ligand can be of formula $P(O$—$Ar)_3$ or $(Ar$—$O)_2$—P-L-P(O—$Ar)_2$ wherein Ar is a $C_6$-$C_{18}$ aryl group which is unsubstituted or substituted with a group selected from the group consisting of $C_1$-$C_6$ alkyl, $C_3$-$C_6$ alkyl, halogen, $C_1$-$C_6$ alkoxyl and $C_6$ aryloxy; and L is a spacer arm selected from the group consisting of $C_1$-$C_6$ alkyl, $C_6$-$C_{12}$ aryl and $C_3$-$C_{10}$ cycloalkyl. Preferably, said phosphorus-bearing ligand can be of formula $P(O$—$Ar)_3$ wherein Ar is a $C_6$ aryl which is unsubstituted or substituted with a methyl, ethyl, methoxy, phenyl, benzyl or cyclohexyl group.

In particular, said phosphorus-bearing ligand can be $P(OPh)_3$, $P(C_6F_5)_3$, $P(o$-MePh$)_3$, $P(o$-OMePh$)_3$.

Alternatively, said one or more ligands also comprise at least one water-soluble monodentate or bidentate phosphorus-bearing ligand comprising at least one functional group $SO_3^-X^+$, $NR_3^+A^-$, $CO_2^-X^+$, X representing Li, Na or K; and A representing Cl, Br or I. Advantageously, said phosphorus-bearing ligand can be of formula $P(Ar)_3$ or $(Ar)_2$—P-L-P$(Ar)_2$ wherein L is a spacer arm selected from the group consisting of $C_1$-$C_6$ alkyl, $C_6$-$C_{12}$ aryl and $C_3$-$C_{10}$ cycloalkyl; and Ar is a $C_6$-$C_{18}$ aryl which is substituted with at least one functional group $SO_3^-X^+$, $NR_3^+A^-$, $CO_2^-X^+$, X representing Li, Na or K, and A representing Cl, Br or I; and optionally substituted with a group selected from the group consisting of $C_1$-$C_6$ alkyl, phenyl, benzyl, $C_3$-$C_6$ cycloalkyl, halogen, $C_1$-$C_6$ alkoxyl and $C_6$ aryloxy.

According to one particular embodiment, step a) also places together a methylated α-, β-, γ-cyclodextrin having an average degree of substitution of between 0.5 and 2.0 or a hydroxylated α-, β-, γ-cyclodextrin having an average degree of substitution of between 0.5 and 0.9. Said methylated α-, β-, γ-cyclodextrin can have an average degree of substitution of between 1.6 and 2.0, or of between 0.9 and 1.6 or of between 0.5 and 0.9. When a cyclodextrin and a water-soluble phosphorus-bearing ligand as mentioned above are used in step a), water is also added in this same step a) in order to create a two-phase medium comprising an organic phase and an aqueous phase. Before the reaction is carried out, the organic phase consists in particular of the compound of formula (I) or (II) according to the present invention and tertiary amine. In this embodiment, the tertiary amine is of formula $NR^8R^9R^{10}$ wherein $R^8$, $R^9$ and $R^{10}$ represent, independently of one another, a $C_4$-$C_{10}$ alkyl. When the process is carried out in the presence of a cyclodextrin, the precatalyst comprises at least one water-soluble monodentate or bidentate phosphorus-bearing ligand as defined above. In addition, the process is carried out under operating conditions which allow the establishment of an emulsion during the stirring and decanting of the reaction products after the stirring has been stopped, preferably decanting of at least one part of the compound according to the present invention. Advantageously, the proportion of cyclodextrin is between 15% and 40% by weight on the basis of the total weight of water, of cyclodextrin and of said one or more compounds of formula (I), preferably of formula (II), as described above, placed together in step a).

The process according to the present invention can also comprise a recycling step when the process is carried out in a two-phase medium. The recycling step comprises degassing the reactor in which the process according to the present invention is carried out, removing the organic phase under a controlled atmosphere, and adding to the reactor the composition A comprising one or more compounds of formula (I) or of formula (II) as described above, tertiary amine $NR^8R^9R^{10}$ and optionally one or more ligands as described above. During this recycling step, the temperature can remain constant, that is to say remain at the temperature at which the hydrohydroxymethylation reaction was carried out, or can be at a temperature above or below the temperature at which the hydrohydroxymethylation reaction was carried out.

According to one particular embodiment of the present invention, said composition A comprising one or more compounds of formula (I), preferably comprising one or more compounds of formula (II), is a vegetable oil having an average number of unsaturations of between 0.5 and 20, advantageously between 0.5 and 15, preferably between 0.5 and 10.

Preferably, said composition A comprising one or more compounds of formula (I), preferably of formula (II), is a vegetable oil having an average number of unsaturations of less than 3.5, advantageously less than 3.4, preferably less than 3.3, more preferentially less than 3.2, in particular less than 3.1, more particularly less than 3.0. Preferably, said vegetable oil has an average number of unsaturations of greater than 0.5, advantageously greater than 1, preferably greater than 1.5, more preferentially greater than 2.0, in particular greater than 2.5. Said vegetable oil can thus have an average number of unsaturations of between 2.0 and 3.2, advantageously between 2.4 and 3.1, preferably between 2.5 and 3.0, in particular between 2.6 and 2.8.

Alternatively, said composition A comprising one or more compounds of formula (I), preferably of formula (II), is a vegetable oil having an average number of unsaturations of between 4 and 10.

Methods
Determination of the Average Number of Unsaturations

The average number of unsaturations is determined by $^1H$ NMR in deuterated chloroform ($CDCl_3$). The NMR analyses are carried out on a Bruker 300 MHz instrument. The average number of unsaturations of a compound is calculated from the value of integration of the $^1H$ NMR signal of the olefin protons located on the fatty acid unit(s) of the compound. The $^1H$ NMR signal of the olefin protons is at 5.3 ppm. If the signal of the olefin protons is covered by one or more other protons, a standardization factor is applied in order to deduce the contribution of the latter proton(s) to the integration value and thus to obtain an integration value corresponding only to the olefin protons.

In the case of the compounds of formula (II) wherein $R^3$ is a hydrogen in any one of the n units, the $^1H$ NMR signal of this hydrogen atom covers the signal of the olefin protons. A standardization factor, denoted FN, is thus calculated according to the equation:

$FN$=(value of the integration of a signal/theoretical number of protons of the corresponding signal)

Figure 2:
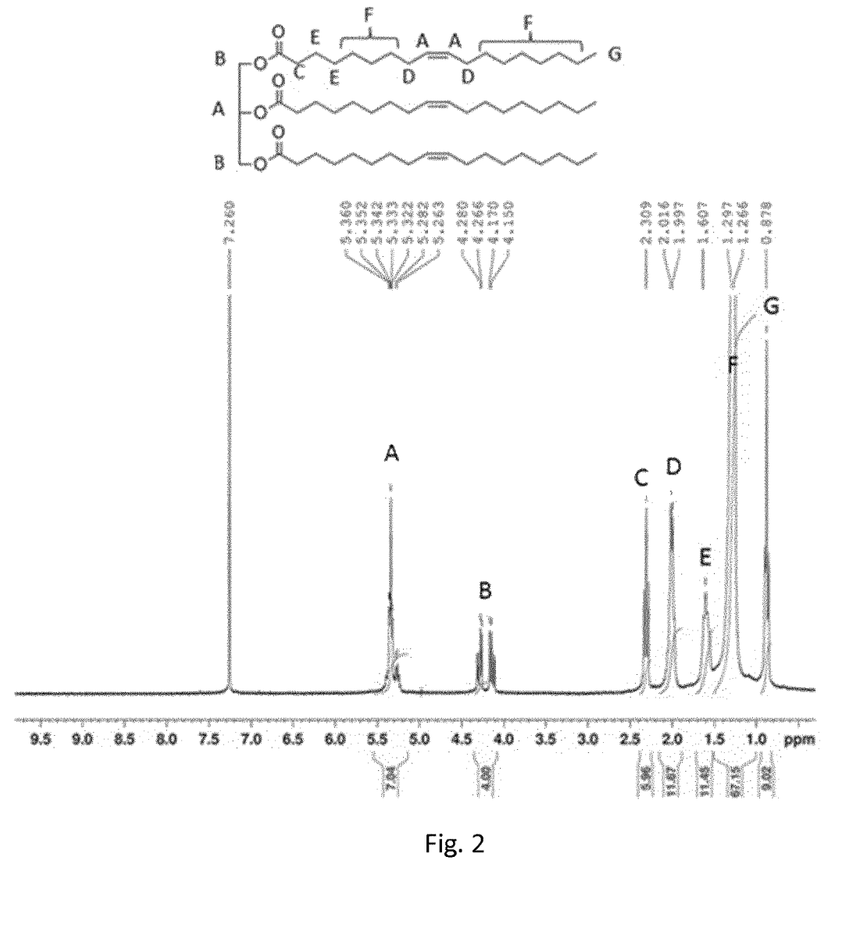
FIG. 2 represents a $^1H$ NMR spectrum of triolein.

For example, for the case of triglycerides, the standardization factor is calculated from the value of integration of the $^1H$ NMR signal corresponding to the protons of the two $CH_2$ groups of glycerol according to the equation $FN=B/4$. FIG. 2 represents the $^1H$ NMR spectrum of triolein. The signal B representative of the signal corresponding to the protons of the two $CH_2$ groups of the glycerol unit has the value of 4 and the standardization factor is thus 1. The glycerol CH proton covers the signal of the olefin protons. The average number of unsaturations is thus deduced from the following equation:

$DBi=(A-FN)/2$ where A corresponds to the value of integration of the signal corresponding to the CH proton of glycerol and the olefin protons (as indicated in FIG. 2), and FN is the standardization factor described above.

When the compound analyzed is not a triglyceride, those skilled in the art will adjust the calculation of the standardization factor FN on the basis of another proton or of another proton group, for example the protons located in position C or D in FIG. 2.

Conversion of the Reaction

The conversion of the reaction is given by the following formula:

Conv. (%)=(($DBi-DBf$)/$DBi$)×100=(($Ai-Af$)/($Ai-FN$))×100 where DBi and DBf are, respectively, the number of initial and final unsaturations and Ai and Af are the integration of the signals A at the beginning and end of the reaction. The signals A correspond to the $^1H$ NMR signals of the olefin protons, as explained above. If the signal of the olefin protons is covered by one or more other protons not corresponding to the olefin protons, a standardization factor FN is applied and calculated as explained above.

Determination of the Alcohol Selectivity

Figure 3:
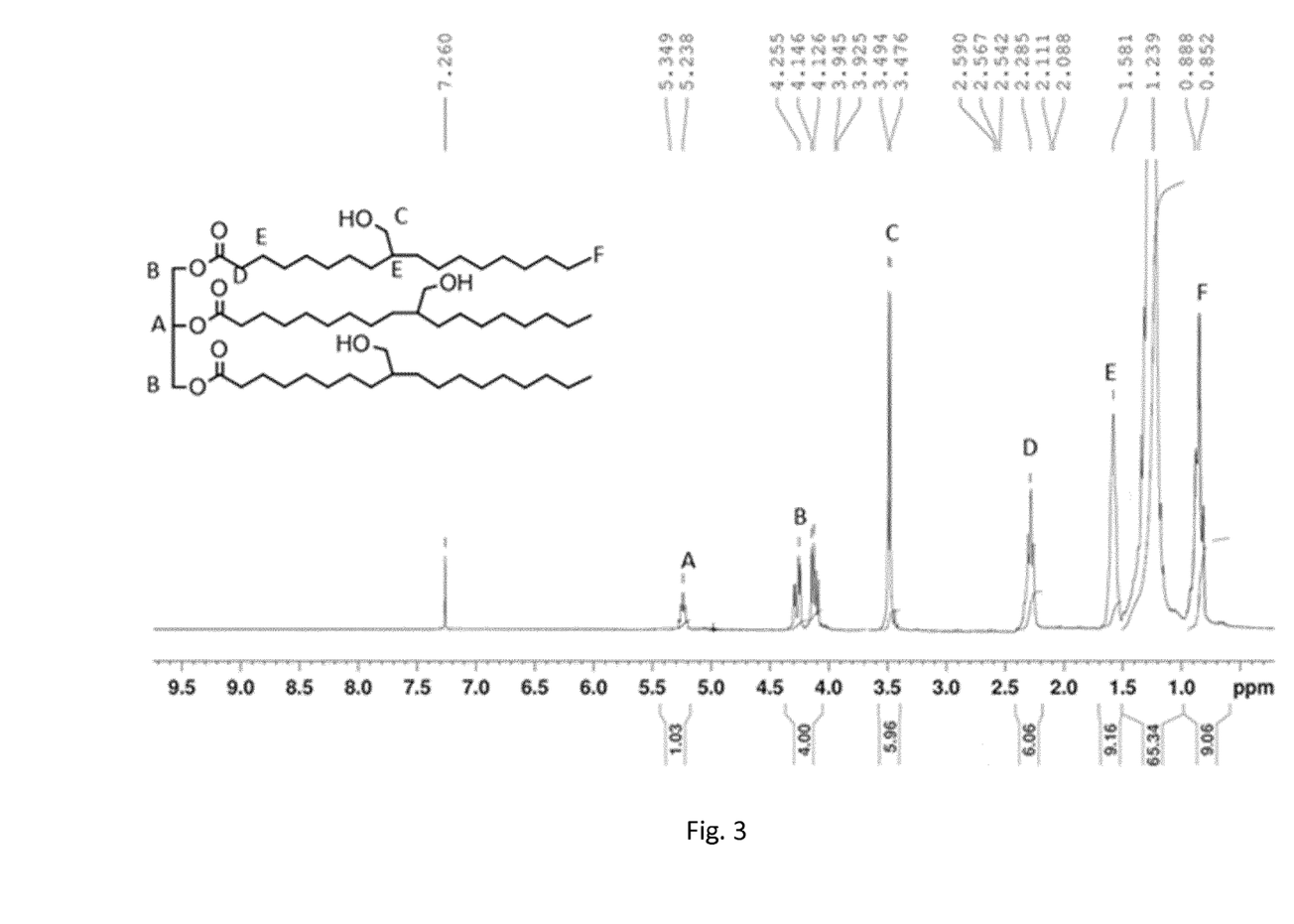
FIG. 3 represents a $^1H$ NMR spectrum of the product obtained by means of the process according to one particular embodiment, starting from triolein.

The selectivities with respect to aldehydes, alcohols and C=C that are hydrogenated, supported by the products resulting from the reaction, are determined by integration of the $^1H$ NMR signals. FIG. 3 represents a $^1H$ NMR spectrum of the product resulting from carrying out the process according to the invention starting from triolein. The signal of the $CH_2$ protons of the hydroxymethylated group (denoted C in FIG. 3) is at 3.54 ppm. The alcohol selectivity of the reaction is given by the formula:

Selec. ($HHM$) (%)=(($C$/($2×FN$))/($DBi-DBf$))×100 where C represents the value of integration of the signal corresponding to the $CH_2$ protons of the hydroxymethylated group, FN represents the standardization factor, and DBi and DBf represent the number of initial and final double bonds.

EXAMPLES

Example 1

1 ml of triolein (1 mmol), 5 ml of toluene, 3.9 mg of $Rh(CO)_2(acac)$ (0.015 mmol) and 3 mmol of amine are mixed in a reactor. The reaction is carried out under a pressure of 80 bar of carbon monoxide and hydrogen (molar ratio 1:1) for 18 hours at 80° C.

Table 1 below reports the results obtained with various tertiary amines.

TABLE 1

Catalytic performances as a function of the tertiary amine

| No. | Amine | Conversion (%) | Aldehyde selec. (%) | Alcohol selec. (%) | Hydrogenation selec. (%) |
| --- | --- | --- | --- | --- | --- |
| 1 | N(Et)$_3$ | 100 | 0 | 93 | 7 |
| 2 | N(Bu)$_3$ | 100 | 0 | 96 | 4 |
| 3 | N(Hex)$_3$ | 100 | 0 | 95 | 5 |
| 4 | N—Me pyrrolidine | 100 | 0 | 95 | 5 |
| 5 | TMEDA | 100 | 8 | 82 | 9 |
| 6 | NMP | 100 | 85 | 0 | 15 |
| 7 | N—Me Pyrrole | 100 | 75 | 0 | 25 |
| 8 | Pyridine | 100 | 78 | 0 | 22 |
| 9 | 1,10-phen | 100 | 76 | 0 | 24 |

Reaction conditions: triolein: 1 mmol (1 ml, 3 mmol of C═C); Rh(CO)$_2$(acac): 0.015 mmol (3.9 mg); toluene: 5 ml; amine: 3 mmol (TMEDA and 1,10-phen: 1.5 mmol); CO/H$_2$ (1:1) pressure: 80 bar; temperature: 80° C.; 18 hours
TMEDA: N,N,N',N'-tetramethylethylenediamine; NMP: N-methyl-2-pyrrolidone; 1,10-phen: 1,10-phenanthroline The results of example 1 demonstrate that the use of tertiary amine allows the "one pot" synthesis of polyols without the use of a co-catalyst or other additives, under relatively mild catalytic conditions. The use of cyclic or non-cyclic aliphatic tertiary amines allows the predominant formation of the desired polyols with an excellent conversion and selectivity. However, the use of nitrogenated heteroaryls (pyridine and pyrrole) or of amides leads to a hydroformylation reaction without a hydrogenation step, thus giving predominantly aldehydes.

Example 2

Example 1 was reproduced using tributylamine as tertiary amine and by varying the carbon monoxide and hydrogen pressure. The reaction time is 6 hours. Table 2 reproduces the results obtained.

TABLE 2

Catalytic performances as a function of the syngas pressure

| No. | Pressure | Conversion (%) | Aldehyde selec. (%) | Alcohol selec. (%) | Hydrogenation selec. (%) |
| --- | --- | --- | --- | --- | --- |
| 10 | 80 | 91 | 39 | 53 | 8 |
| 11 | 100 | 100 | 20 | 75 | 5 |

Reaction conditions: triolein: 1 mmol (1 ml, 3 mmol of C═C); Rh(CO)$_2$(acac): 0.015 mmol (3.9 mg); toluene: 5 ml; tributylamine: 3 mmol; CO/H$_2$ (1:1); temperature: 80° C.; 6 hours The total CO/H$_2$ syngas pressure has an influence on the hydrohydroxymethylation conversions and also on the final-product selectivities. When the total pressure increases, the conversion and the alcohol selectivity also increase. It should also be noted that, the more the pressure increases, the more the C═C hydrogenation selectivity decreases. However, if the pressure is substantially increased, the first hydroformylation step is promoted, followed by the step of hydrogenation of newly formed aldehydes, the hydrogenation of the substrate then having to be slower.

Example 3

Example 1 was reproduced in the presence of tributylamine for 6 hours while varying the reaction temperature. Table 3 reproduces the results obtained.

TABLE 3

Catalytic performances as a function of the temperature

| No. | Temperature (° C.) | Conversion (%) | Aldehyde selec. (%) | Alcohol selec. (%) | Hydrogenation selec. (%) |
| --- | --- | --- | --- | --- | --- |
| 12 | 80 | 91 | 39 | 53 | 8 |
| 13 | 110 | 99 | 2 | 89 | 9 |
| 14 | 140 | 100 | 0 | 93 | 7 |

Reaction conditions: triolein: 1 mmol (1 ml, 3 mmol of C═C); Rh(CO)$_2$(acac): 0.015 mmol (3.9 mg); toluene: 5 ml; tributylamine: 3 mmol; CO/H$_2$ (1:1) pressure: 80 bar; 6 hours Above 80° C., the triglyceride conversion increases, accompanied by a strong activity of hydrogenation of the aldehydes produced and surprisingly limiting the hydrogenation of the carbon-carbon double bonds of the substrate.

Example 4

Example 4 aims to determine the influence of the CO/H$_2$ molar ratio on the hydrohydroxymethylation reaction. Example 1 was reproduced with triethylamine as tertiary amine. The reaction time was established at 6 hours. The results are reproduced in table 4 below.

TABLE 4

Influence of the CO/H$_2$ ratio

| No. | CO/H$_2$ ratio | Amine | Conversion (%) | Aldehyde selec. (%) | Alcohol selec. (%) | Hydrogenation selec. (%) |
| --- | --- | --- | --- | --- | --- | --- |
| 15 | 1:1 | N(Et)$_3$ | 94 | 12 | 81 | 7 |
| 16 | 1:2 | N(Et)$_3$ | 95 | 1 | 93 | 6 |

Reaction conditions: triolein: 1 mmol (1 ml, 3 mmol of C═C); Rh(CO)$_2$(acac): 0.015 mmol (3.9 mg); toluene: 5 ml; amine: 3 mmol; total CO/H$_2$ pressure: 80 bar; temperature: 80° C.; 6 hours Increasing the hydrogen partial pressure has a surprising effect on the alcohol formation. The use of a 1:2 molar ratio of CO/H$_2$ makes it possible to reach stoichiometric reaction proportions (one molecule of CO used for two molecules of hydrogen) and makes the catalytic system more hydrogenating so as to rapidly achieve the expected polyols.

Example 5

The present process for preparing polyols was applied starting from a natural vegetable oil. Table 5 reproduces the results obtained.

TABLE 5

Application to vegetable oils

| No. | Oils | Conv. (%) | Average number of unsaturations | Aldehyde selec. (%) | Alcohol selec. (%) | Hydrogenation selec. (%) | Isomerization selec. (%) |
| --- | --- | --- | --- | --- | --- | --- | --- |
| 17 | Olive | 94 | 2.78 | 2 | 90 | 8 | 0 |

Reaction conditions: oil: 1 mmol (1 ml); Rh(CO)$_2$(acac): 0.015 mmol (3.9 mg); toluene: 5 ml; triethylamine: 3 mmol; CO/H$_2$ (1:1) pressure: 80 bar; temperature: 80° C.

It emerges from these results that the process according to the invention applies to vegetable oils, that is to say to compositions comprising triglycerides of different structures.

Example 6

Example 1 was reproduced in the presence of a self-emulsifying system. The addition of cyclodextrin, and in particular of CRYSMEB® (CDs methylated in position 2 and having a degree of substitution per glucosidic unit (DS) of 0.8) makes it possible to form a surfactant complex at the oil/water interface. This interface-stabilizing complex makes it possible to emulsify the two-phase system and to increase the interface between the two media. The process is carried out in the presence of a precatalyst also comprising a water-soluble phosphine-type ligand such as the trisodium salt of triphenylphosphine trisulfonated in the meta position (TPPTS). The results are reproduced in table 6 below.

TABLE 6

| Process in self-emulsifying medium | | | | |
| --- | --- | --- | --- | --- |
| No. | Amine | Conversion (%) | Aldehyde selec. (%) | Alcohol selec. (%) | Hydrogenation selec. (%) |
| 18 | N(Bu)$_3$ | 92 | 3 | 92 | 4 |
| 19 | N(Oct)$_3$ | 94 | 3 | 91 | 5 |

Reaction conditions: triolein: 1 mmol (1 ml, 3 mmol of C=C); Rh(CO)$_2$(acac): 0.015 mmol (3.9 mg); TPPTS: 0.075 mmol (42 mg); water: 8 ml; CRYSMEB: 2 mmol (2.3 g); amine: 3 mmol; CO/H$_2$ (1:1) pressure: 80 bar; temperature: 80° C.; 18 hours.

The use of cyclodextrin in a self-emulsifying medium makes it possible to efficiently convert the initial C=C unsaturations into alcohol function, this being with very good selectivity and while limiting the formation of hydrogenation product.

The terms and descriptions used herein are proposed by way of illustration only and do not constitute limitations. Those skilled in the art will recognize that many variations are possible within the spirit and scope of the invention as described in the claims which follow, and their equivalents; in said claims, all the terms should be understood in their broadest sense unless otherwise indicated.

The invention claimed is:

1. A process for preparing polyols from a composition A, said composition A comprising one or more compounds of formula (I)

(I)

wherein $R^1$, $R^2$, $R^3$, $R^4$, $R^5$, $R^6$ and $R^7$ are, independently of one another, and for $R^3$ and $R^7$ independently for each of the n units, selected from the group consisting of H, —OR$^{15}$, $C_1$-$C_{10}$ alkyl which is unsubstituted or substituted with one or more —OR$^{15}$ groups, $C_6$-$C_{12}$ aryl which is unsubstituted or substituted with one or more —OR$^{15}$ groups, or $C_3$-$C_{10}$ cycloalkyl which is unsubstituted or substituted with one or more —OR$^{15}$ groups, and a group of formula (Ia)

(Ia)

$R^{15}$ represents H or $C_1$-$C_{10}$ alkyl which is unsubstituted or substituted with one or more —OH groups;

a, b, x and y are independently of one another, independently for each group of formula (Ia), independently for each [(CH$_2$)$_a$—C=C—(CH$_2$)$_b$]$_r$ unit and independently for each [(CH$_2$)$_x$—C=C—(CH$_2$)$_y$]$_p$ unit, an integer between 0 and 20 r is an integer between 1 and 10 p is an integer between 1 and 10 n is an integer between 1 and 7;

said process comprising a step a) of placing together, with stirring and under an atmosphere of hydrogen and of carbon monoxide:

at least one precatalyst which is a complex comprising a transition metal chosen from column 9 of the periodic table, a tertiary amine, or a non-quaternary ammonium salt thereof, of formula NR$^8$R$^9$R$^{10}$ wherein R$^8$, R$^9$ and R$^{10}$ represent, independently of one another, a $C_1$-$C_{10}$ alkyl, a $C_6$-$C_{12}$ aryl or a $C_3$-$C_{10}$ cycloalkyl, or R$^8$ and R$^9$ form, together with the nitrogen atom to which they are attached, a heterocycle comprising four, five or six ring members, said composition A comprising said compound of formula (I).

2. The process as claimed in claim 1, characterized in that step a) is carried out at a temperature between 70° C. and 180° C.

3. The process as claimed in claim 1, characterized in that said at least one compound of formula (I) is of formula (II)

(II)

wherein a, b, x and y are, independently of one another, independently for each group of formula (Ia), independently for each [(CH$_2$)$_a$—C=C—(CH$_2$)$_b$]$_r$ unit and independently for each [(CH$_2$)$_x$—C=C—(CH$_2$)$_y$]$_p$ unit, an integer between 0 and 20 p is, independently for each [(CH$_2$)$_x$—C=C—(CH$_2$)$_y$]$_p$ unit, an integer between 1 and 5;

r is, independently for each [(CH$_2$)$_a$—C=C—(CH$_2$)$_b$]$_r$ unit, an integer between 1 and 5;

$R^1$, $R^2$, $R^3$, $R^4$ and $R^5$ are, independently of one another, and for $R^3$ independently for each of the n units, selected from the group consisting of H, —OR$^{15}$, $C_1$-$C_{10}$ alkyl which is unsubstituted or substituted with one or more —$OR^{15}$ groups, and a group of formula (Ia) as described above, $R^{15}$ represents H or $C_1$-$C_{10}$ alkyl which is unsubstituted or substituted with one or more —OH groups;

n is an integer between 1 and 4.

4. The process as claimed in claim 3, characterized in that said at least one compound of formula (I) is of formula (II) wherein a and x can be, independently of one another, independently for each $[(CH_2)_x\!-\!C\!=\!C\!-\!(CH_2)_y]_p$ unit and independently for each $[(CH_2)_a\!-\!C\!=\!C\!-\!(CH_2)_b]_r$ unit, an integer between 1 and 12;

b and y can be, independently of one another, independently for each $[(CH_2)_x\!-\!C\!=\!C\!-\!(CH_2)_y]_p$ unit and independently for each $[(CH_2)_a\!-\!C\!=\!C\!-\!(CH_2)_b]_r$ unit, an integer between 0 and 12;

$R^1$, $R^2$, $R^3$, $R^4$ and $R^5$ are a hydrogen;

p is 1, 2 or 3 independently for each $[(CH_2)_x\!-\!C\!=\!C\!-\!(CH_2)_y]_p$ unit;

r is 1, 2 or 3 independently for each $[(CH_2)_a\!-\!C\!=\!C\!-\!(CH_2)_b]_r$ unit;

n is 1.

5. The process as claimed in claim 1, characterized in that the tertiary amine is of formula $NR^8R^9R^{10}$ wherein $R^8$, $R^9$ and $R^{10}$ represent, independently of one another, a $C_1$-$C_{10}$ alkyl, or $R^8$ and $R^9$ form, together with the nitrogen atom to which they are attached, an azetidine, diazetidine, pyrrolidine, imidazolidine or pyrazolidine heterocycle.

6. The process as claimed in claim 1, characterized in that the precatalyst is a complex comprising rhodium as transition metal and one or more ligands.

7. The process as claimed in claim 1, characterized in that it is carried out under pressure of a hydrogen and carbon monoxide atmosphere, said pressure being between 50 bar and 200 bar.

8. The process as claimed in claim 1, characterized in that the molar ratio between the carbon monoxide and the hydrogen is between 2:1 and 1:10.

9. The process as claimed in claim 1, characterized in that the molar ratio between the amine and the transition metal is greater than 20.

10. The process as claimed in claim 1, characterized in that said composition A comprising one or more compounds of formula (I) is a vegetable oil having an average unsaturation number of less than 3.5.

11. The process as claimed in claim 1, characterized in that a, b, x and y are independently of one another, independently for each group of formula (Ia), independently for each $[(CH_2)_a\!-\!C\!=\!C\!-\!(CH_2)_b]_r$ unit and independently for each $[(CH_2)_x\!-\!C\!=\!C\!-\!(CH_2)_y]_p$ unit, are between 0 and 15.

12. The process as claimed in claim 1, characterized in that r is between 1 and 5 inclusive.

13. The process as claimed in claim 1, characterized in that p is between 1 and 5 inclusive.

14. The process as claimed in claim 1, characterized in that x and y are each independently between 1 and 10 inclusive.

15. The process as claimed in claim 5, characterized in that $R^8$, $R^9$ and $R^{10}$ represent, independently of one another, $C_1$-$C_{10}$ alkyl, or $R^8$ and $R^9$ form, together with the nitrogen atom to which they are attached, a pyrrolidine.

16. The process as claimed in claim 6, characterized in that the at least one of said one or more ligands is at least one of CO, acetylacetonate, cyclooctadiene, norbornene or acetate.

17. The process as claimed in claim 8, characterized in that the molar ratio between the carbon monoxide and the hydrogen is between 1:1 and 1:5.

18. The process as claimed in claim 9, characterized in that the molar ratio between the amine and the transition metal is greater than 50.

19. The process as claimed in claim 10, characterized in that the average unsaturation number of less than 3.4.

* * * * *